United States Patent [19]

Leschek et al.

[11] Patent Number: 4,563,643
[45] Date of Patent: Jan. 7, 1986

[54] EDDY CURRENT PROXIMITY SENSOR FOR USE IN A HOSTILE TURBINE ENVIRONMENT

[75] Inventors: Walter C. Leschek, Monroeville; Robert C. Miller, Penn Hills, both of Pa.

[73] Assignee: Westinghouse Electric Corp., Pittsburgh, Pa.

[21] Appl. No.: 403,431

[22] Filed: Jul. 30, 1982

[51] Int. Cl.$^4$ .................. G01B 7/14; H01F 27/02
[52] U.S. Cl. ..................... 324/207; 336/92
[58] Field of Search ............ 324/207, 208, 262; 336/30, 65, 92

[56] References Cited

U.S. PATENT DOCUMENTS

| | | | |
|---|---|---|---|
| 2,049,924 | 8/1936 | Pugh | 175/83 |
| 2,830,261 | 4/1958 | Estelle | 324/446 |
| 3,132,299 | 5/1964 | Hochschild | 324/238 |
| 3,152,303 | 10/1964 | Lary et al. | 324/204 |
| 3,336,525 | 8/1967 | Church | 336/30 |
| 3,378,763 | 4/1968 | Hastings | 324/224 |
| 3,467,358 | 9/1969 | Zablotsky | 253/77 |
| 3,491,289 | 1/1970 | Petrini | 324/207 |
| 3,521,159 | 7/1970 | Morrow | 324/207 |
| 3,634,799 | 1/1972 | Strauch | 336/92 |
| 3,680,363 | 8/1972 | Hetz et al. | 73/71.4 |
| 3,707,671 | 12/1972 | Morrow | 336/179 X |
| 3,911,731 | 10/1975 | Walker et al. | 73/71.4 |
| 3,932,813 | 1/1976 | Gallant | 324/164 |
| 3,989,408 | 11/1976 | Jaetnes | 415/14 |
| 4,042,876 | 8/1977 | Visioli, Jr. | 324/207 |
| 4,067,661 | 1/1978 | Gebhart | 415/118 |
| 4,180,329 | 12/1979 | Hildebrand | 356/375 |
| 4,196,390 | 4/1980 | Pitkin | 324/262 |

Primary Examiner—Gerard R. Strecker
Assistant Examiner—Walter E. Snow
Attorney, Agent, or Firm—D. Schron

[57] ABSTRACT

An eddy-current sensor having a thimble shaped alumina housing into which is positioned first and second coils wound about an insulating coil support. A Kovar sealing ring seals the alumina housing to a metallic base member to which is secured a protective tube carrying an electrical cable which makes electrical connection with the coils. A multifaceted nut secured to the metallic shielding of the cable nestles within a complementary shaped insulating member to prevent the cable from being twisted or withdrawn from the sensor thus maintaining electrical integrity.

11 Claims, 6 Drawing Figures

EDDY CURRENT PROXIMITY SENSOR FOR USE IN A HOSTILE TURBINE ENVIRONMENT

BACKGROUND OF THE INVENTION

1. Field of the Invention

The invention in general relates to sensors for measuring distance to metallic objects, and particularly to a rugged sensor of the eddy-current variety.

2. Description of the Prior Art

Eddy-current sensors are well known and operate on the principle that the impedance of an ac-excited electrical coil is subject to change as the coil is brought in close proximity to a metallic object. For a given coil location, geometry and excitation frequency, the coil's inductance and resistance change is a function of the electrical conductivity, magnetic permeability, and geometry of the metallic object.

Instruments utilizing the eddy-current sensor are well known for measuring displacement or vibration in various types of machinery. By way of example these sensors are utilized to monitor the blading arrangement in a steam turbine as described in co-pending application, Ser. No. 413,638 filed Aug. 31, 1982, now U.S. Pat. No. 4,518,917, and assigned to the same assignee as the present invention. Commercially available sensors utilized in the hostile turbine environment are subject to failure due to various causes such as vibration induced cracking of the sensor housing, erosion of sensor parts due to abrasive damage from water droplets which may impact at a velocity as high as 1,200 feet per second, and electrical wire breakage due to rough handling during installation.

The sensor of the present invention obviates the deficiencies of the prior art sensors so as to allow its use in environments where other sensors have failed.

SUMMARY OF THE INVENTION

The sensor of the present invention is a rugged relatively small unit for substantially inobtrusive insertion into existing machinery systems to be monitored. The sensor includes a hollow non-metallic housing having a front face and a cylindrical side wall integral therewith terminating in a flanged base. The housing is preferably of a ceramic material and a sensor has been constructed with a housing made of alumina of approximately 96% purity.

A non-metallic coil support is positioned within the housing and includes coil means wound on the support. A metallic base support member is included and has a circumferential flange portion as well as a hollow stem portion. A retaining ring is provided and has a shoulder portion sealed, such as by soldering, to the flange base portion of the housing, with the ring also including a flange portion sealed, such as by welding, to the flanged portion of the base support member thus providing for a hermetically sealed unit which will remain sealed in the presence of severe vibration and high-temperature saturated steam. A multiwire shielded electric cable extends through the stem portion of the base support member and is electrically connected with the coil means.

A protective tube member sealed to the hollow stem portion of the base support member provides a conduit for the electric cable and may be connected to other conduit for leading the cable out of the machinery under test.

In a preferred embodiment the hollow stem portion is multifaceted and receives a hollow complementary multifaceted stem portion of an insulating member. A multifaceted nut is fastened to the shielding of the electric cable and seats within the multifaceted interior of the insulating member with such arrangement preventing twisting of the cable to an extent that might breaK the connections between the cable and coil means.

DESCRIPTION OF THE PREFERRED EMBODIMENT

Figure 1:
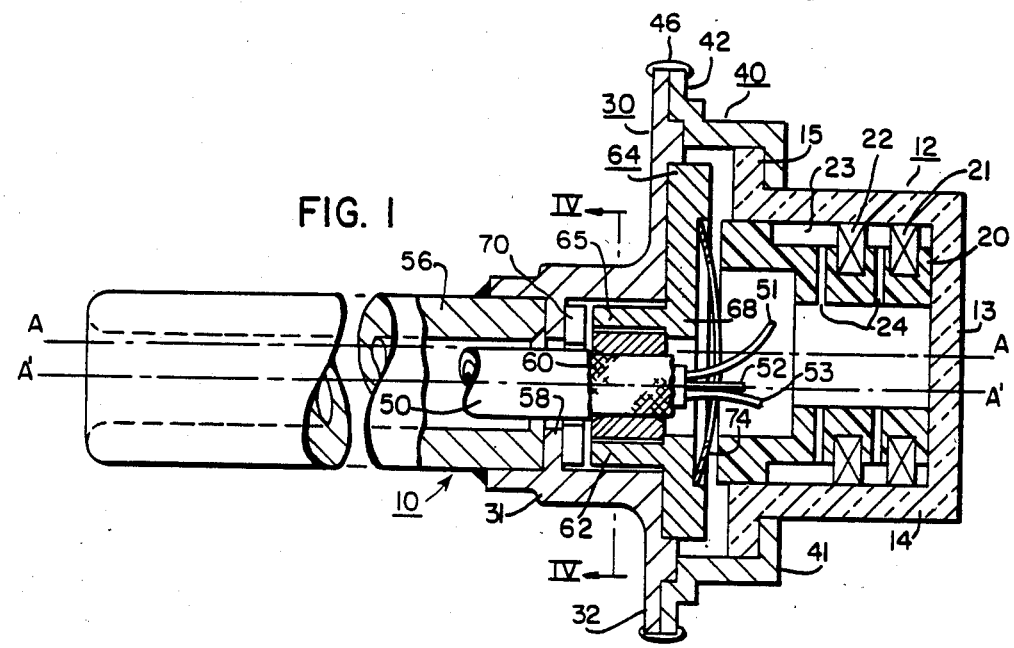
FIG. 1 is a sectional view through the sensor, in accordance with one embodiment of the present invention.

Sensor 10 of FIG. 1 is a proximity sensor of the eddy-current variety and includes at the front portion thereof a non-metallic housing 12 having a front face 13 and a cylindrical side wall portion 14 integral therewith terminating in a flanged base 15. For use in a hostile environment such as encountered in the interior of a low pressure steam turbine, it is imperative that the housing 12, and in particular the front face 13 be resistant to abrasive damage from water droplets impacting at a normal velocity in the order of 1,200 feet per second. Additionally the housing must be capable of withstanding the elevated temperatures encountered during normal operation. Therefore in a preferred embodiment housing 12 is fabricated from a dense ceramic material such as alumina (aluminum oxide).

Disposed within housing 12 is a coil support 20 having at least one coil 21 wound thereon, and in a preferred embodiment another coil 22 is included. The use of a second coil in such sensors is well known for the purpose of nullifying the effects of certain temperature induced coil impedance changes, so as to provide for more accurate readings. Slots 23 in the support 20, in conjunction with apertures 24 allow the ends of the coils to be brought into the interior of support 20 so that electrical connection may be made to them.

Coil support 20 is of a non-metallic material and may be fabricated from a plastic such as polyimide which is durable, strong, and dimensionally stable at elevated temperatures.

A metallic base support member 30, such as of stainless steel, includes an apertured stem portion 31 and a circumferential flange portion 32 which is instrumental in the hermetic sealing of the sensor unit.

This sealing is accomplished with the provision of a retaining ring 40 having a shoulder portion 41 which slips over the outside of housing 20 and engages the flanged base 15. At its other end, ring 40 includes a flange portion 42 which mates with the circumferential flange portion 32 of the base support member 30 for sealing engagement therewith.

Figure 2:
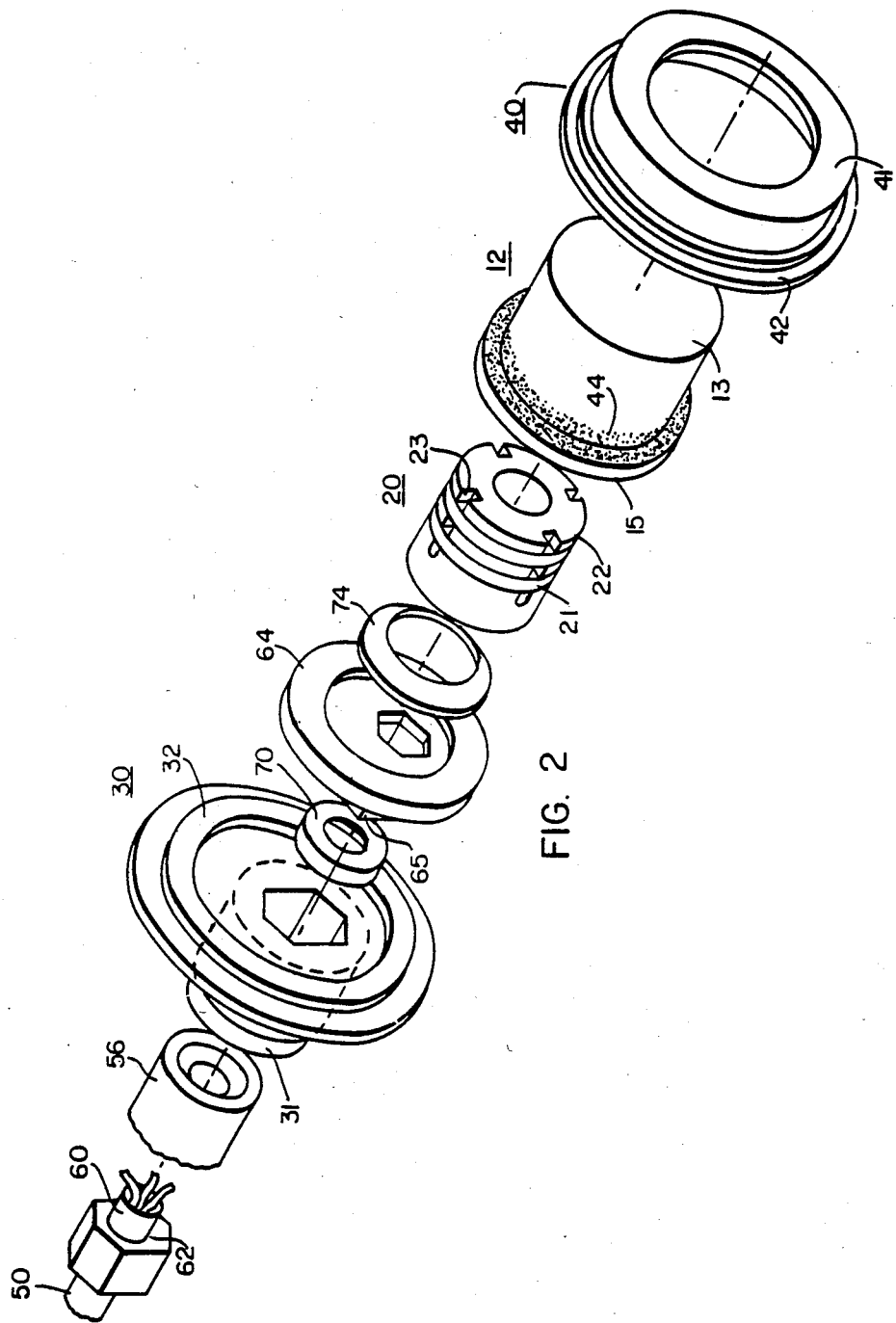
FIG. 2 is an exploded view of the sensor of FIG. 1.

Retaining ring 40 is preferably made of Kovar metal to allow for very good thermal expansion matching with alumina housing 12 and fairly good thermal expansion matching with the base support member 30. Shoulder portion 41 of the ring is placed into sealing engagement with the flange base 15 of the alumina housing with the sealing being accomplished by means of a high temperature solder, by way of example. In this respect the alumina housing is provided with a metalized surface, such as nickel plated molymanganese metallization, as indicated by numeral 44 (FIG. 2) to provide for a soldering seal to the alumina. The seal between the Kovar retaining ring and the base support member may be effected by means of a peripheral weld 46.

Figure 3:
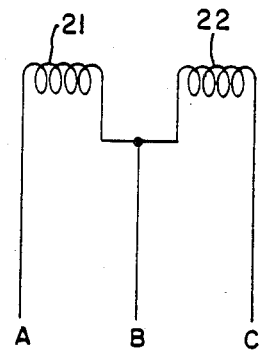
FIG. 3 is an electrical diagram showing the electrical connection between the coils of FIG. 1.

Coils 21 and 22 may in one arrangement be electrically connected as indicated in FIG. 3. Accordingly, an electric cable 50 is provided and includes three wires 51, 52, and 53 for making soldered connection with points A, B and C of the coil arrangement of FIG. 3. Cable 50 is positioned within a protective tube 56 which fits into the apertured stem portion 31 of the base support member 30 and secured thereto such as by welding. Axial movement of the protective tube into the aperture stem portion is limited by means of the reduced diameter portion 58 inside the stem.

In the course of mounting in a turbine, or other type of installation, the sensor 10 may be subject to rough handling. If the cable is accidently twisted or pulled, there is danger that the electrical connection to the coils may be broken or weakened to an extent where they would break during operation. Accordingly the present invention includes an arrangement for preventing such occurrences.

As part of this protective arrangement, cable 50 which is of the type having a braided metallic shield 60 has a metallic nut 62 affixed thereto such as by soldering to the braided metallic shield. In order to prevent the metallic shield and nut from contacting the metal stem portion of the base support member 30 and causing electrical ground-loop noise during operation, the nut is positioned within an insulating member 64, and more particularly within an apertured stem portion 65 thereof. Insulating member 64 may, like coil support 20, be of a polyimide plastic.

Figure 4:
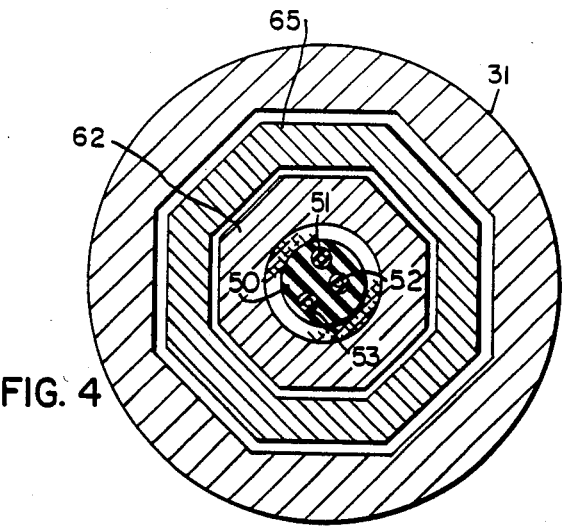
FIG. 4 is a view along the lines IV—IV of FIG. 1.

The interior of stem portion 65 is multifaceted to mate with the exterior faces of nut 62. By way of example the nut and interior surface of the stem potion 65 may include six surfaces defining a hexagonal shape, as best illustrated in FIG. 4 which is a view along line IV—IV of FIG. 1. In order to prevent the insulating member 64 from twisting within the stem of base support member 30 the complementary mating surfaces thereof, that is the outside surface of stem portion 65 and inside surface of stem portion 31 (to the right of reduced diameter portion 58 as seen in FIG. 1) are also hexagonally shaped, as seen in FIG. 4.

Nut 62 is prevented from being moved into the interior of coil support 20 by virtue of a reduced diameter lip portion 68 at the forward end of insulating member 64. The nut is prevented from being pulled out of position by the inclusion of an insulating washer 70 having a central aperture through which the cable 50 passes, with the aperture diameter being such as to prevent passage of nut 62.

During measuring operations, it is imperative that the coils do not axially move within the housing 12. One way of providing immobility is to machine the parts to exacting tolerances. A less expensive and easier way to maintain the coils in a fixed position relative to face 13 is with the inclusion of a biasing means such as a wave spring washer 74 which contacts insulating member 64 and forces coil support 20 into the desired rigid engagement.

Figure 5:
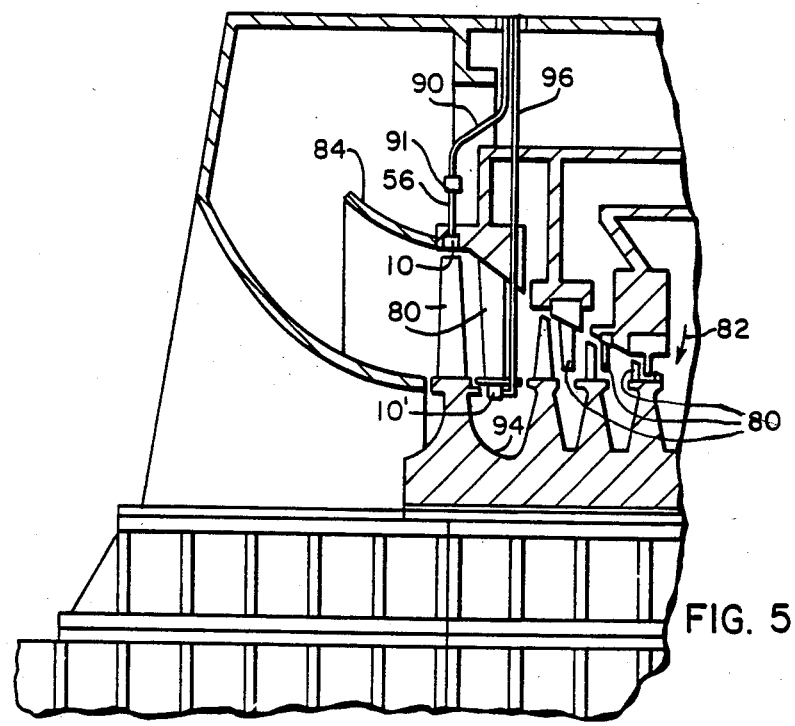
FIG. 5 illustrates the sensor in a turbine environment.

FIG. 5 illustrates a typical use for the sensor as may be applied to a low pressure steam turbine. Steam enters the blading arrangement 80 in the direction of arrow 82 and exits via flow guide 84. Sensors may be mounted for monitoring the last blade row at the flow guide location and for this purpose a plurality of such sensors are disposed in the flow guide radially around the blades. A typical arrangement is described in the aforementioned co-pending application. Sensor 10 is illustrated in FIG. 5 as being mounted in flow guide 84 and tubing 56 is connected to additional protective tubing 90 via coupling 91 with such additional protective tubing being bent around the interior parts of the turbine and conducted to the exterior thereof whereby electrical connection may be made to monitoring equipment.

Another sensor 10' is illustrated as being positioned for obtaining an indication of axial movement of rotor 94. Tubing 96 may be connected to sensor 10' for providing a protective path for the cable to the turbine exterior.

Figure 6:
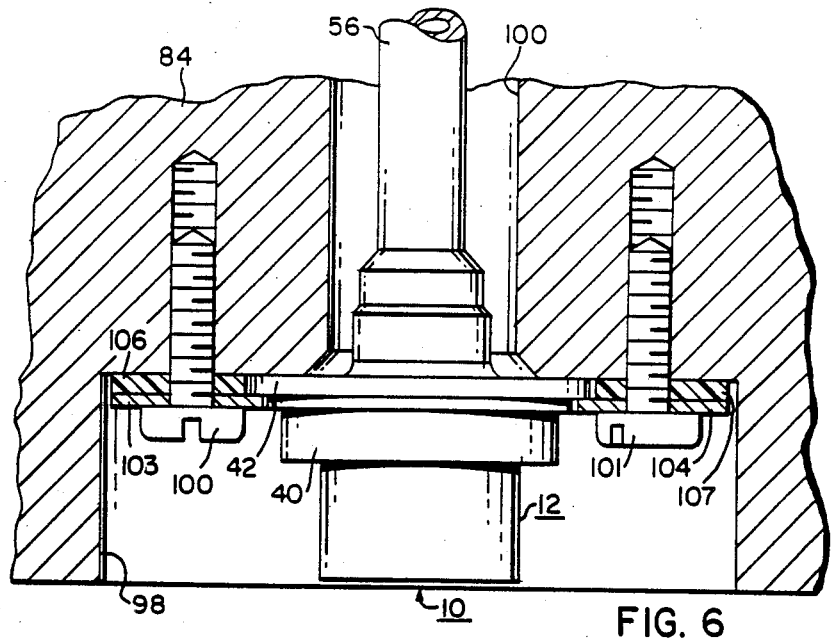
FIG. 6 illustrates the mounting arrangement of FIG. 5 in somewhat more detail.

FIG. 6 is a sectional view through the flow guide 84 illustrating the mounting of sensor 10 in somewhat more detail. An aperture 98 is machined into flow guide 84 and is of sufficient size and shape to accommodate the sensor 10 as well as the means for affixing sensor 10 to the flow guide. An aperture 100 is also provided for accommodating the protective tube 56.

One way of affixing sensor 10 to the interior of aperture 98 is with the inclusion of fasteners such as machine screws 100 and 101, in conjunction with washers such as stainless steel washers 103 and 104 which abut the flange portion 42 of retaining ring 40. Washers 103 and 104 in turn rest upon respective washers 106 and 107 which may be of teflon.

Once the sensor is in the position as illustrated in FIG. 6 and before final tightening of fasteners 100 and 101 it may be desired to laterally move the sensor to a limited degree thereby changing its relative positioning with respect to the blade row. One way of accomplishing this is by designing the sensor such that the coaxial central axis A (FIG. 1) of the housing 12 and coil support 20 is offset from the central axis A' of the protective tube 56 carrying cable 50. During installation, protective tube 56 may be manually rotated which would result in rotation of axis A about axis A' and impart limited lateral movement of the coil arrangement.

What is claimed is:
1. A proximity sensor comprising:
(a) a hollow non-metallic housing having a central axis and having a front face and a cylindrical side wall integral with said front face and terminating in a flanged base;
(b) a non-metallic coil support positioned within said housing;
(c) coil means wound on said coil support;
(d) a base support member having a circumferential flange portion and a hollow stem portion;
(e) a retaining ring having a shoulder portion sealed to said flanged base of said housing and having a flange portion sealed to said flange portion of said base support member; and
(f) a multiwire electrical cable extending through said stem portion of said base support member and electrically connected with said coil means;

(g) a protective tube lying along an axis and having one end positioned within said hollow stem portion of said base support member;
(h) said electric cable being positioned within said tube;
(i) said tube axis being offset from said housing central axis.

2. Apparatus according to claim 1 wherein
(a) said housing is alumina.

3. Apparatus according to claim 1 wherein:
(a) said coil means includes first and second electrically connected coils.

4. Apparatus according to claim 1 wherein:
(a) said housing and said coil support are coaxial; and
(b) said coils are displaced one behind the other along said coaxial arrangement.

5. Apparatus according to claim 1 which includes:
(a) spring means bearing against said coil support and urging it into contact with the inside surface of said front face.

6. Apparatus according to claim 1 wherein:
(a) said retaining ring is of Kovar and is welded to said flange portion of said base support member.

7. Apparatus according to claim 1 which includes:
(a) means to prevent said cable from being pulled out of said tube.

8. Apparatus according to claim 7 wherein:
(a) said sensor is positioned within a turbine housing; and which includes,
(b) additional protective tubing connected between said tube and said housing.

9. A proximity sensor comprising:
(a) a hollow non-metallic housing having a front face and a cylindrical side wall integral therewith terminating in a flanged base;
(b) a non-metallic coil support positioned within said housing;
(c) coil means wound on said coil support;
(d) a base support member having a circumferential flant portion and a hollow stem portion;
(e) a retaining ring having a shoulder portion sealed to said flanged base of said housing and having a flange portion sealed to said flange portion of said base support member; and
(f) a multiwire electrical cable extending through said stem portion of said base support member and electrically connected with said coil means;
(g) an insulating member including a hollow stem portion positioned within the hollow stem portion of said base support member;
(h) the interior of said hollow stem portion of said base support member including a multifaceted surface;
(i) the interior of said hollow stem portion of said insulating member including a complementary multifaceted surface to prevent relative twisting of said stem portions.

10. Apparatus according to claim 9 wherein:
(a) the interior of said hollow stem portion of said insulating member includes a multifaceted surface and which additionally includes;
(b) a multifaceted nut secured to said electric cable and seated within said hollow stem portion of said insulating member to prevent relative twisting of said cable.

11. Apparatus according to claim 10 wherein:
(a) said electric cable includes a metallic sheath;
(b) said nut being secured to said metallic sheath.

* * * * *